United States Patent
Barral et al.

(10) Patent No.: US 12,367,972 B1
(45) Date of Patent: Jul. 22, 2025

(54) SURGICAL ROBOTIC SYSTEM CONFIGURATION

(71) Applicant: Verily Life Sciences LLC, South San Francisco, CA (US)

(72) Inventors: Joëlle Barral, Mountain View, CA (US); James Shuma, San Jose, CA (US); Michal Levin, Sunnyvale, CA (US)

(73) Assignee: Verily Life Sciences LLC, Dallas, TX (US)

( * ) Notice: Subject to any disclaimer, the term of this patent is extended or adjusted under 35 U.S.C. 154(b) by 912 days.

(21) Appl. No.: 16/949,239

(22) Filed: Oct. 21, 2020

Related U.S. Application Data

(60) Provisional application No. 62/923,672, filed on Oct. 21, 2019.

(51) Int. Cl.
| | | |
|---|---|---|
| *G16H 40/40* | (2018.01) | |
| *A61B 34/32* | (2016.01) | |
| *A61B 90/00* | (2016.01) | |
| *G05B 19/4155* | (2006.01) | |
| *G16H 10/60* | (2018.01) | |

(Continued)

(52) U.S. Cl.
CPC ............ *G16H 40/40* (2018.01); *A61B 34/32* (2016.02); *A61B 90/06* (2016.02); *G05B 19/4155* (2013.01); *G16H 10/60* (2018.01); *G16H 20/40* (2018.01); *G16H 40/63* (2018.01); *G16H 50/30* (2018.01); *G16H 50/70* (2018.01);

(Continued)

(58) Field of Classification Search
CPC ........ G16H 40/40; G16H 40/63; G16H 10/60; G16H 20/40; G16H 50/30; G16H 50/70; G16H 70/20; A61B 34/32; A61B 90/06; G05B 19/4155; G05B 2219/45117
See application file for complete search history.

(56) References Cited

U.S. PATENT DOCUMENTS

| 8,120,301 B2 | 2/2012 | Goldberg et al. | |
|---|---|---|---|
| 11,779,412 B2 * | 10/2023 | Ida .......................... | A61B 34/10 606/1 |

(Continued)

FOREIGN PATENT DOCUMENTS

| CN | 102066057 | 5/2011 |
|---|---|---|
| JP | 2015118556 | 6/2015 |

(Continued)

*Primary Examiner* — Tammie K Marlen
*Assistant Examiner* — Maria Catherine Anthony
(74) *Attorney, Agent, or Firm* — Kilpatrick Townsend & Stockton LLP

(57) ABSTRACT

Systems and methods for configuring and instructing movement of a surgical device using configuration data from previous surgeries are described herein. Robotic surgical systems described herein include robotic arms with interchangeable surgical tools. The kinematics of the robotic arms are compared against configuration data from previous procedures and differences between the kinematics and the configuration data are identified. The configuration data also includes simulations of robotic surgical systems throughout a procedure. Potential collisions or complications from present and future configurations are identified. The differences and instructions for resolving the differences and potential collisions are presented to a user for correction.

22 Claims, 8 Drawing Sheets

(51) Int. Cl.
    *G16H 20/40*    (2018.01)
    *G16H 40/63*    (2018.01)
    *G16H 50/30*    (2018.01)
    *G16H 50/70*    (2018.01)
    *G16H 70/20*    (2018.01)
    *G16H 50/20*    (2018.01)

(52) U.S. Cl.
    CPC ... *G16H 70/20* (2018.01); *G05B 2219/45117* (2013.01); *G16H 50/20* (2018.01)

(56) References Cited

U.S. PATENT DOCUMENTS

| | | |
|---|---|---|
| 2011/0306986 A1 | 12/2011 | Lee et al. |
| 2012/0113285 A1 | 5/2012 | Baker et al. |
| 2018/0028931 A1 | 2/2018 | Bear et al. |
| 2018/0350148 A1 | 12/2018 | George |
| 2019/0000569 A1 | 1/2019 | Crawford et al. |
| 2019/0206564 A1* | 7/2019 | Shelton, IV ............ A61M 1/79 |
| 2020/0383734 A1* | 12/2020 | Dahdouh ............... A61B 34/30 |

FOREIGN PATENT DOCUMENTS

| | | | |
|---|---|---|---|
| KR | 100956762 | 5/2010 | |
| KR | 101936130 | 1/2019 | |
| WO | WO-2017076886 A1 * | 5/2017 | ............ A61B 34/10 |

\* cited by examiner

SURGICAL ROBOTIC SYSTEM CONFIGURATION

CROSS-REFERENCE TO RELATED APPLICATIONS

This application claims priority to U.S. Provisional Patent Application No. 62/923,672, filed Oct. 21, 2019, titled "Surgical Robotic System Configuration," the entirety of which is hereby incorporated by reference.

BACKGROUND

In recent years, robotic surgeries have become increasingly popular because of their advantages over traditional human-operated open surgeries. Surgical tools used in robotic surgeries enable a human surgeon to have improved levels of dexterity, range of motion, and precision. In most robotic surgical systems, these tools are connected to robotic arms and interchangeable depending on the surgery to be performed.

SUMMARY

Various examples are described including systems, methods, and devices relating to configuring surgical robots.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method, including: receiving, by a computing device, data corresponding to a surgical procedure associated with a robotic surgical system, the robotic surgical system including a plurality of robotic arms. The computer-implemented method also includes determining an initial configuration for each of the plurality of robotic arms by at least: accessing a dataset of configurations corresponding to a plurality of surgical procedures and selecting the initial configuration based on the surgical procedure and the dataset of configurations, the initial configuration defining an initial position and orientation and an initial tool selection for each robotic arm of the plurality of robotic arms before beginning the surgical procedure. The computer-implemented method also includes receiving kinematic data corresponding to a state of each of the plurality of robotic arms. The computer-implemented method also includes determining a difference between the state of each of the plurality of robotic arms and the initial configuration based on the kinematic data. The computer-implemented method also includes providing instructions to a user, based on the difference, to move each robotic arm of the plurality of robotic arms into the respective initial position and orientation. The computer-implemented method also includes determining a plurality of configurations for each of the plurality of robotic arms during the surgical procedure based on a dataset of expected robotic arm configurations for the surgical procedure, individual robotic arm configurations defining one or more of (1) positions, (2) orientations, or (3) tool selections for the plurality of robotic arms during the surgical procedure. The computer-implemented method also includes determining, during the surgical procedure, that a configuration of the robotic surgical system differs from at least one expected robotic arm configuration of the plurality of expected robotic arm configurations. The difference may be greater than a predetermined threshold in some examples. The computer-implemented method also includes generating a configuration notification relating to the configuration differing from the at least one expected robotic arm configuration. Other embodiments of this aspect include corresponding computer systems, apparatus, and computer programs recorded on one or more computer storage devices, each configured to perform the actions of the methods.

One general aspect includes a robotic surgical system including: a plurality of robotic arms, a user interface, one or more processors, and one or more non-transitory computer-readable media including processor-executable instructions that, when executed by the one or more processors, cause the one or more processors to perform the following steps. The steps include receiving data corresponding to a surgical procedure performable by the plurality of robotic arms and determining an initial configuration for each of the plurality of robotic arms by at least accessing a dataset of configurations corresponding to a plurality of surgical procedures and selecting the initial configuration based on the surgical procedure and the dataset of configurations, the initial configuration defining an initial position, orientation, and an initial tool selection for each robotic arm of the plurality of robotic arms before beginning the surgical procedure. The steps also include receiving kinematic data corresponding to a state of each of the plurality of robotic arms and determining a difference between the state of each of the plurality of robotic arms and the initial configuration based on the kinematic data. The steps also include providing instructions to a user, based on the difference, for movement of each robotic arm of the plurality of robotic arms into the initial configuration. The steps further include determining a plurality of configurations for each of the plurality of robotic arms during the surgical procedure based on a dataset of expected configurations for the surgical procedure, individual robotic arm configurations defining one or more of (1) positions, (2) orientations, or (3) tool selections for the plurality of robotic arms during performance of the surgical procedure. The steps further include determining, during the surgical procedure, that a configuration of the plurality of robotic arms differs from at least one expected configuration of the plurality of configurations and generating a configuration notification for presentation at the user interface, the configuration notification relating to the configuration differing from the at least one expected configuration.

One general aspect includes a computer-implemented method, including: receiving, by a computing device, data corresponding to a surgical procedure associated with a robotic surgical system, the robotic surgical system including a plurality of robotic arms. The computer-implemented method also includes accessing a dataset of configurations corresponding to a plurality of surgical procedures and selecting an initial tool configuration based on the surgical procedure, the initial tool configuration defining an initial tool selection for the plurality of robotic arms before beginning the surgical procedure. The computer-implemented method further includes providing instructions to a user, based on the initial tool configuration, the instructions including steps for connecting interchangeable tools to the plurality of robotic arms based on the initial tool configuration. Other embodiments of this aspect include corresponding computer systems, apparatus, and computer programs recorded on one or more computer storage devices, each configured to perform the actions of the methods.

Another general aspect includes a robotic surgical system, including: a plurality of robotic arms, a user interface, one or more processors, and one or more non-transitory computer-readable media including processor-executable instructions that, when executed by the one or more processors, cause the one or more processors to perform the following steps. The steps include receiving, via the user interface, data corresponding to a surgical procedure associated with the robotic surgical system and accessing a dataset of configurations corresponding to a plurality of surgical procedures. The steps also include selecting a configuration of the dataset of configurations based on the surgical procedure. The steps further include determining an initial tool configuration based on the configuration, the initial tool configuration defining an initial tool selection of the plurality of robotic arms before beginning the surgical procedure. The steps further include instructing, via the user interface, connection of interchangeable tools to the plurality of robotic arms based on the initial tool configuration.

Another general aspect includes a computer-implemented method, including: receiving, by a computing device, data corresponding to a surgical procedure associated with a robotic surgical system, the robotic surgical system including a plurality of robotic arms. The computer-implemented method also includes accessing a dataset of configurations based on the surgical procedure, the dataset of configurations defining at least one of an orientation, a position, or a tool selection for each of the plurality of robotic arms during the surgical procedure. The computer-implemented method also includes receiving kinematic data corresponding to a configuration of the plurality of robotic arms. The computer-implemented method also includes determining when the configuration of the plurality of robotic arms differs from the dataset of configurations by comparing the dataset of configurations to the configuration of the plurality of robotic arms. The computer-implemented method further includes generating a deviation notification when the configuration differs from the dataset of configurations. Other embodiments of this aspect include corresponding computer systems, apparatus, and computer programs recorded on one or more computer storage devices, each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
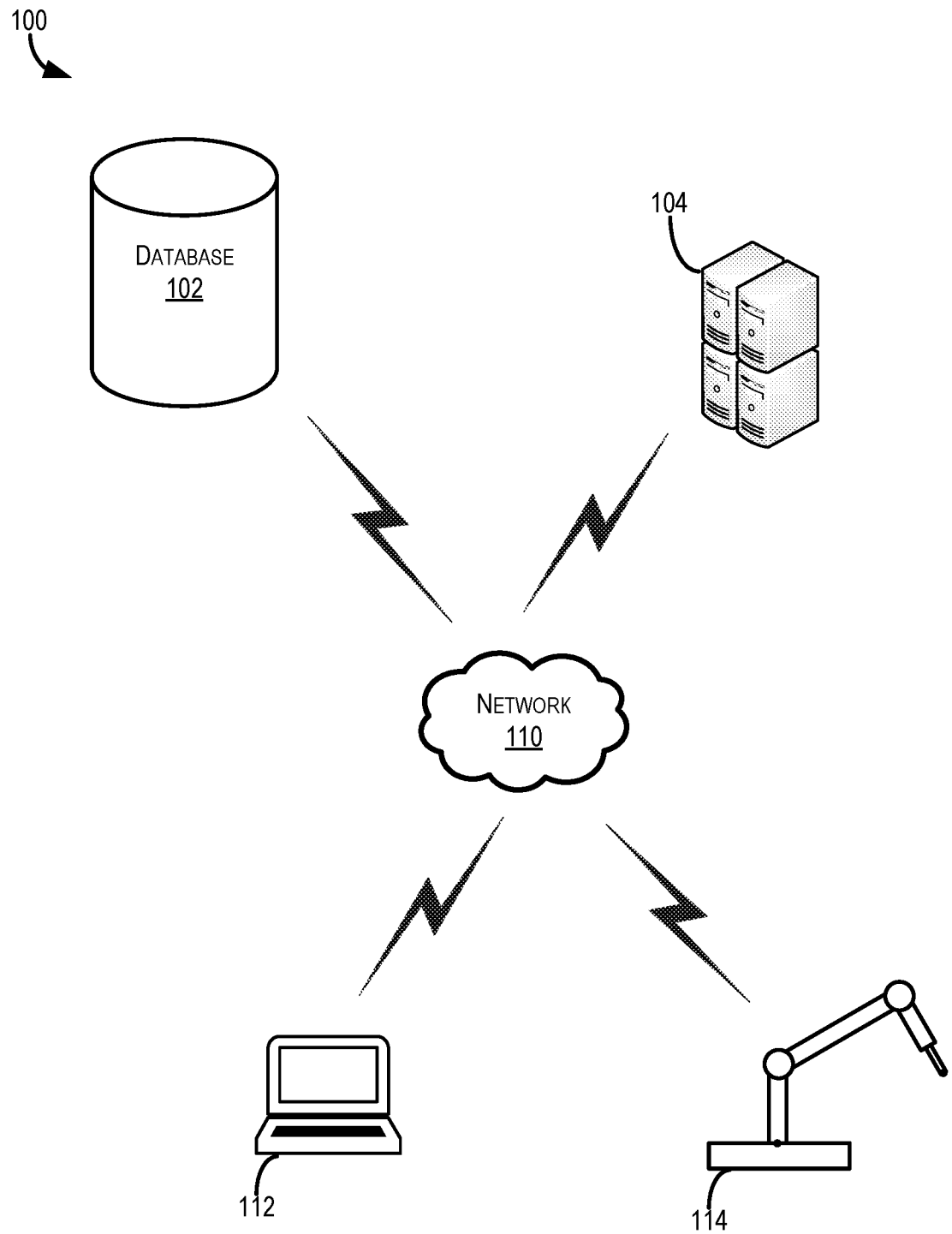
FIG. 1 illustrates a block diagram illustrating an example system for configuring a surgical robot, according to at least one example.

Examples are described herein in the context of configuring a surgical robot at the start of and throughout surgical procedures. Those of ordinary skill in the art will realize that the following description is illustrative only and is not intended to be in any way limiting. For example, the techniques described herein may be used to initially assign tools to robotic arms and position arms to start a surgical procedure as well as configure orientations of the robotic arms during the surgical procedure. Though examples and techniques are described with reference to surgical robot configurations, the methods and systems described herein may be implemented in other robotic systems such as robotic systems used in assembly processes or other user-controlled robotic systems. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In robotic surgical systems, initial configuration of the robotic device may be critical to ensure consistency, safety, and success of surgical procedures. The initial configuration includes both connecting proper surgical tools to robotic arms as well as initially positioning the robotic arms. During a surgical procedure, it is also important to keep robotic arm movements within certain ranges, such as to reduce the risk of collision with other objects such as patient anatomy or external objects in the operating room. The techniques described herein increase the speed and accuracy for configuring a robotic surgical system by accessing previous surgical procedure data and using such historical information to generate an initial configuration for the robotic surgical system. Additionally, during the procedure, the surgeon may be assisted by the system, reducing the chances of surgeon error and improving patient outcomes.

In an illustrative example, a robotic surgical system includes one or more robotic arms each having a surgical tool connected to it. A camera, e.g., an endoscope, is connected to one of the robotic arms to capture images or videos of a surgical procedure performed using the surgical tools. The robotic surgical system also includes a surgeon console for managing operation of the robotic arms (e.g., enabling a surgeon to operate the surgical tools). The robotic surgical system also includes a computer system having software loaded thereon to enable some techniques described herein that are controllable through the surgeon console. For example, the computer system may include software to perform image segmentation to identify the surgical tools within images of the surgical obtained by the camera and provided at the surgeon console.

In this illustrative example, the robotic surgical system includes a tool assignment module. The tool assignment module provides instructions to a user regarding which interchangeable tools to connect to the robotic arms at the start of and at different times throughout a surgical procedure. The tool assignment module reviews data stored according to the type of surgical procedure to be performed and compiles a list of surgical tools, tool assignments, and times during the procedure to connect the surgical tools. The display device displays instructions to the user, such as a surgeon or assistant describing which interchangeable tool should be attached to each of the robotic arms. During the procedure, the instructions from the tool assignment module also provide updated tool assignment information as additional tools are required for the procedure.

The robotic surgical system also includes a configuration module that aids the user in positioning the robotic arms before or during a surgical procedure. The configuration module compares the present configuration of the robotic arms to historical configuration data describing previous positions of robotic arms in previous similar surgeries and presents instructions to the user to adjust the robotic arms to better match the historical configuration data, such as based on statistical patterns in past surgical procedures that may be related to patient characteristics, surgical outcomes, etc. The configuration data includes positions and orientations for each of the robotic arms at each stage of the surgical procedure and may also include information about which tools should be attached. In some cases, the instructions to the user from the configuration module may help to train a new user to use the robotic surgical system. The instructions may also be useful for the user to ensure that portions of the robotic arms outside of the field of view of a camera will avoid collisions with each other or with other objects such as patient anatomy or surgical tables and instruments. These instructions will help avoid collisions in the future during the surgical procedure, and prevent unworkable or difficult positioning of the robotic arms.

The systems and methods described herein increase the speed and accuracy for configuring a robotic surgical system by accessing previous surgical procedure data and using such historical information to generate an initial configuration for the robotic surgical system thereby reducing the need for the user to determine the initial configuration. Additionally, during the procedure, the surgeon may be assisted by the system, which may provide instructions to the user to aid in positioning or movement of the robotic surgical system, reducing the chances of surgeon error and improving patient outcomes. In some cases, the instructions to the user from the configuration module may also be used to train a new user to use the robotic surgical system and help them become familiar or comfortable with the robotic surgical system or a new procedure. The instructions may also be useful for the user to ensure that portions of the robotic arms outside of the field of view of a camera will avoid collisions with each other or with other objects such as patient anatomy or surgical tables and instruments, further increasing the safety of procedures performed using the robotic surgical system.

This illustrative example is given to introduce the reader to the general subject matter discussed herein and the disclosure is not limited to this example. The following sections describe various additional non-limiting examples and techniques relating to configuring a surgical robot for a surgical procedure.

Turning now to the figures, FIG. 1 illustrates a block diagram of a system 100 for configuring a surgical device 114, according to at least one example. The system 100 includes computing device 104, surgical device 114, surgical console 112, and database 102. The surgical device 114 includes any suitable number of robotic arms, as described in additional detail with respect to FIG. 2. The computing device 104, the database 102, and the surgical console 112 may be in network communication with each other as shown through network 110. As described in additional detail with respect to FIGS. 4 and 5, the computing device 104 executes software to enable some of the example processes described herein. In some examples, the computing device 104 may be the surgical console 112 in some examples or may be integrated as a part of the surgical console 112. The surgical console 112 is the interface device to the robotic surgical system that a user uses to control the surgical device 114 and to view the display 118. In some examples, it may include other components, such as described below with respect to FIG. 2.

The computing device 104 communicates, via the network 110, with the database 102 to access configuration data for each of the robotic arms based on the procedure selected. As described in additional detail with respect to FIG. 4, the computing device 104 receives kinematic data from the surgical device 114 describing the present state of the robotic arms including their orientation and position. The computing device 104 further communicates with the surgical console 112 and causes the display of the surgical console 112 to display instructions to a user regarding a proper configuration of the surgical device 114. In some examples the database 102 is part of the computing device 104, such as a memory component or internal database of the computing device 104.

Figure 5:
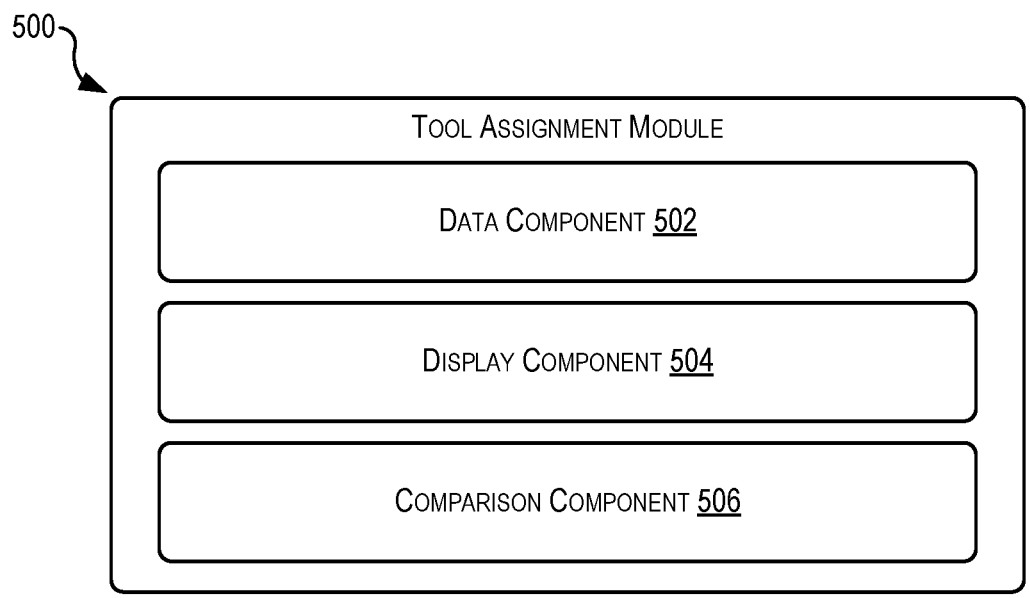
FIG. 5 illustrates a simplified block diagram depicting elements for assigning tools to robotic arms of a surgical robot, according to at least one example.

As described in additional detail with respect to FIG. 5, the computing device 104 communicates with the database 102 and the surgical console 112 to access a set of tool configuration data for the procedure and then display, at the surgical console 112, instructions to the user regarding which surgical tools to attach to the robotic arms.

The computing device 104, as described herein, is any suitable electronic device (e.g., personal computer, handheld device, server computer, server cluster, virtual computer, etc.) configured to execute processor-executable instructions to perform operations such as those described herein. The components of the system 100 are connected via one or more communication links with the network 110. The network 110 includes any suitable combination of wired, wireless, cellular, personal area, local area, enterprise, wide-area, virtual, or other suitable network.

Figure 2:
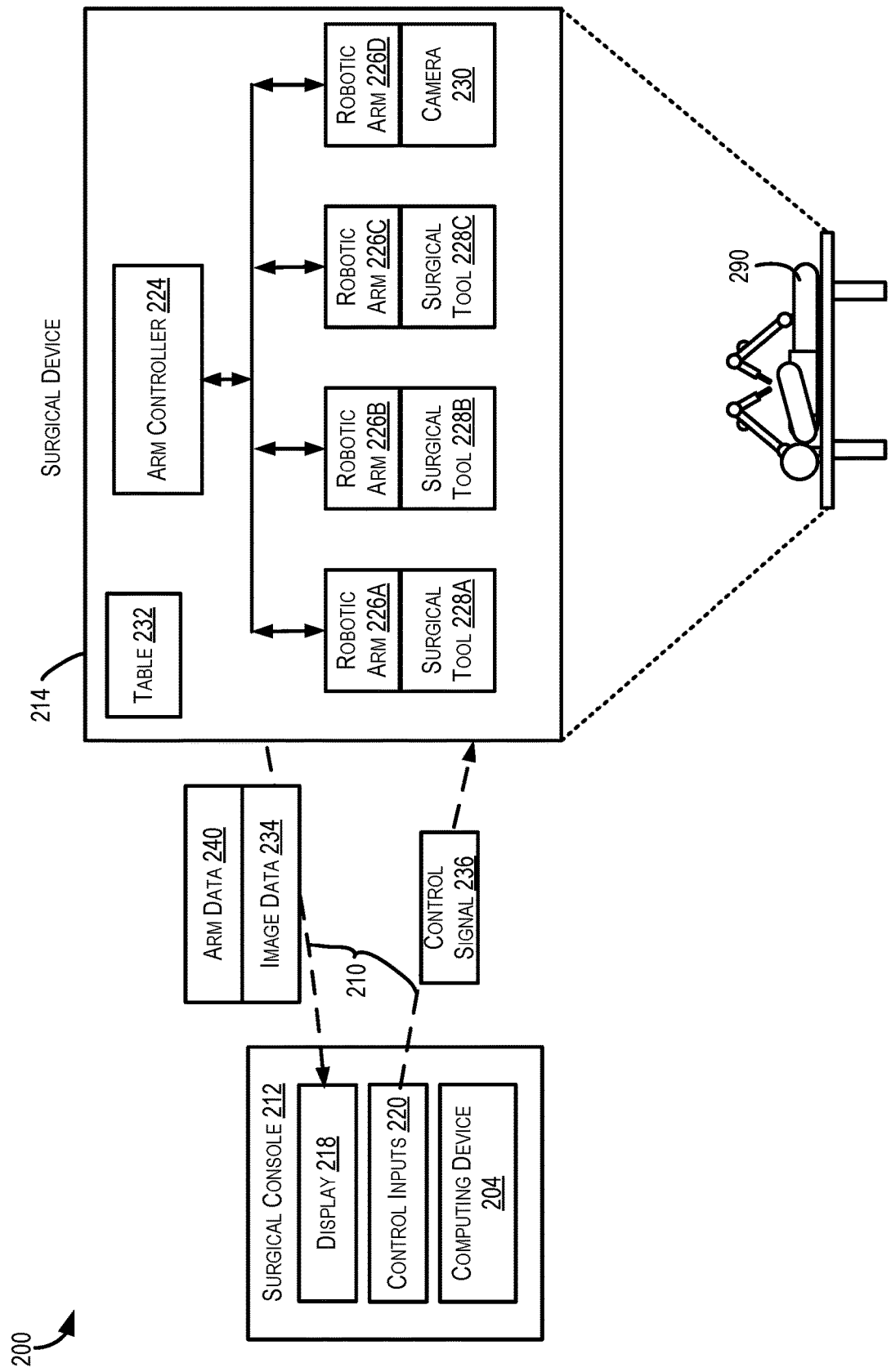
FIG. 2 illustrates an example system for configuring a surgical robot, according to at least one example.

FIG. 2 illustrates a system 200 for configuring surgical device 214, according to at least one example. In the system 200, the surgical device 214 is configured to perform a surgical procedure on a patient 290. The system 200 also includes a surgical console 212 connected to the surgical device 214 and configured to be operated by a surgeon to control and monitor the surgeries performed by the surgical device 214. The system 200 might include additional stations (not shown in FIG. 2) that can be used by other personnel in the operating room, for example, to view surgical information, video, etc., sent from the surgical device 214. The surgical device 214, the surgical console 212, and other stations can be connected directly or through the network 210, such as a local-area network ("LAN"), a wide-area network ("WAN"), the Internet, a controller-area network ("CAN"), or any other networking topology known in the art that connects the surgical device 214, the surgical console 212 and other stations.

The surgical device 214 can be any suitable robotic system that can be used to perform surgical procedures on the patient 290. The surgical device 214 includes one or more robotic arms 226A-D (which may be referred to herein individually as a robotic arm 226 or collectively as the robotic arms 226) connected to a base such as a table 2232. The robotic arms 226 may be manipulated by control inputs 220, which may include one or more user interface devices, such as joysticks, knobs, handles, or other rotatable or translatable devices to effect movement of one or more of the robotic arms 226. The robotic arms 226A-D may be equipped with one or more surgical tools 228A-D to perform aspects of a surgical procedure. For example, the robotic arms 226A-C may be equipped with surgical tools 228A-C, (which may be referred to herein individually as a surgical tool 228 or collectively as the surgical tools 228). The surgical tools 228 can include, but are not limited to, tools to grasp, to hold, or to retract objects, such as forceps, graspers and retractors, tools to cut and suture, such as needle drivers, scalpels and scissors, and other tools that can be used during a surgery. Each of the surgical tools 228 can be controlled by the surgeon through the surgical console 212 including the control inputs 220.

Different surgical devices may be configured for particular types of surgeries, such as cardiovascular surgeries, gastrointestinal surgeries, gynecological surgeries, transplant surgeries, neurosurgeries, musculoskeletal surgeries, etc., while some may have multiple different uses. As a result, different types of surgical robots, including those without robotic arms, such as for endoscopy procedures, may be employed according to different examples. It should be understood that while only one surgical device 214 is depicted, any suitable number of surgical devices may be employed within system 200.

The surgical device 214 is also equipped with one or more cameras 230, such as an endoscope camera, configured to provide a view of the operating site to guide the surgeon during the surgery. In some examples, the camera 230 can be attached to one of the robotic arms 226D. In some examples, the camera 230 can be attached to a mechanical structure of the surgical device 214 that is controlled separately from the robotic arms 226 or is stationary with respect to the surgical device 214.

The surgical device 214 includes an arm controller 224. The arm controller 224 controls the positioning and movement of the robotic arms 226 based on control signals 236 from the surgical console 212 generated by the control inputs 220. The arm controller 224 may be within or part of the computing device 204.

The surgical console 212 includes a display 218 to provide a feed of image data 234 from the camera 230 as well as notifications and instructions from the computing device 204. The computing device 204 may be part of the surgical console 212 or may be remote from the surgical console 212. The image data 234 is transferred to the surgical console 212 over the network 210 along with arm data 240 describing the position of each of the robotic arms 226. The computing device 204 described in FIG. 2 is shown included in the surgical console 212 but may also be located remotely of the surgical console 212 as described above.

The computing device 204 presents the image data 234 received from camera 230 on the display 218. The computing device 204 also generates notifications or graphical interface elements which appear on the display 218 to instruct the user according to methods described below. The notifications may also include auditory or haptic feedback notifications.

During setup of the system 200, including connection of the surgical tools 228 to the robotic arms 226 and positioning of the robotic arms 226, the computing device 204 determines a set of surgical tools 228 needed for the procedure. The set of surgical tools 228 is determined by the computing device 204 based on tool data from database 202 and the procedure to be performed by the surgical device 214. The computing device 204 may select the tools based on a surgical plan, by referencing previous surgeries and the surgical tools used in those previous surgeries. The tool data includes the identities of surgical tools 228 as well as the robotic arms 226 to which each should be connected. The tool data may further include procedure steps or temporal markers within the surgery at which points in time the surgical tool 228 may be interchanged. The computing device 204 may also determine a set of surgical tools 228 needed throughout the procedure, including any that are changed out partway through the procedure. As the tool assignments change, the computing device 204 may produce a notification at the display 218 of the surgical console 212 instructing a user to change the surgical tools 228 based on the data from the database 202. For example, at the start of the procedure, a first robotic arm 226A may have a grasper connected to it and a second robotic arm 226B may have a cutting tool connected. At a point partway through the procedure, the computing device 204 may inform the user to remove the cutting tool and instead attach a different tool, such as a spreader.

The computing device 204 also interfaces with the surgical device 214 to assist a user in preoperative positioning and intraoperative positioning of robotic arms 226. The computing device 204 is also configured to access configuration data from database 202 based on the surgical procedure to be performed by the surgical device 214 and also to receive kinematic data describing the position and orientation of the robotic arms 226. The configuration data describes or relates to the specific surgical tools connected to the robotic arms 226 while the kinematic data describes the positions and orientations of the joints and linkages of the robotic arms 226 at the present time. For example, the computing device 204 may determine from the configuration data that a different tool is needed and then the computing device 204 may inform a user to connect a grasper to a first robotic arm 226A and a cutting tool to a second robotic arm 226B. The computing device 204 generates instructions to position or re-position the robotic arms 226 based on current differences as well as predicted future configurations of the robotic arms 226 as compared against the database 202. The computing device 204 generates these instructions by comparing the kinematic data against historical kinematic data as well as against simulated kinematic data generated based on previous surgical procedures. The simulated kinematic data may be based on the present kinematic data of the surgical device 214 as well as positions and orientations of the joints and linkages of the robotic arms 226 throughout the previous surgical procedures. The processes carried out by the computing device 204 are described in greater detail with respect to processes 600, 700, 800, and 900 below. The computing device 204 may further be configured to provide a position score for each of the robotic arms 226 indicating how well the kinematic data matches the historical kinematic data stored on database 202. The computing device 204 may further be configured to access data from the database 202 and store data on the database 202. The computing device 204 may be configured to adjust the data received from the database 202 based on patient characteristics, such as body mass index ("BMI") or patient dimensions, or characteristics such as height or gender. The computing device 204 may further be configured to adjust kinematic data from a current or recently completed procedure based on the patient characteristics to normalize the data into a universal or standardized dataset which may be adjusted for later procedures based on new patient dimensions.

Figure 3:
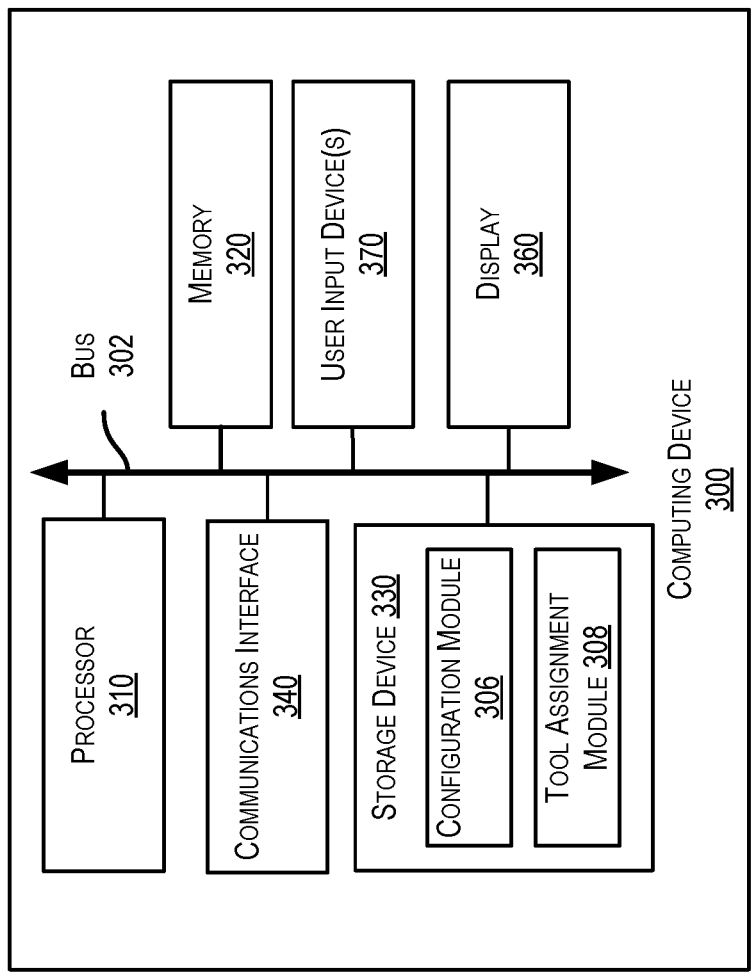
FIG. 3 illustrates a simplified block diagram depicting an example architecture for implementing the techniques described herein, according to at least one example.

Referring now to FIG. 3, FIG. 3 shows computing device 300 suitable for use in example systems or methods to improve robotic surgical safety via video processing, according to at least one example. For example, computing device 300 may be the computing device 104, 204 of FIG. 1 or 2, respectively. Computing device 300 includes a processor 310 which is in communication with the memory 320 and other components of the computing device 300 using one or more communications buses 302. The processor 310 is configured to execute processor-executable instructions stored in the memory 320 to provide setup and instructions for the user to position the surgical device 114 according to different examples, such as part or all of the example processes 600, 700, 800, and 900 described below with respect to FIGS. 6, 7, 8, and 9. The computing device 300, in this example, also includes one or more user input devices 370, such as a keyboard, mouse, touchscreen, microphone, etc., to accept user input. The computing device 300 also includes a 360 display to provide visual output to a user.

It should be understood that although FIGS. 1 and 2 illustrate various components of the systems 100, 200, some elements of the system 100, such as the database 202 or the configuration module 306 or tool assignment module 308, that are included in the computing device 104 or in communication over the network 110, one or more of these modules may be implemented in different ways within the system 100. For example, the functionality described above need not be separated into discrete modules, or some or all of such functionality may be located on a computing device separate from the surgical device 114, the surgical console 112, or the computing device 104 such as a central controlling device connected to the surgical device 114 directly or through the network 110 and configured to control the components of the system 100.

The computing device 300 can include or be connected to one or more storage devices 330 that provides non-volatile storage for the computing device 300. The storage devices 330 can store system or application programs and data used by the computing device 300, such as modules implementing the functionalities provided by the configuration module 306 and the tool assignment module 308. The storage devices 330 might also store other programs and data not specifically identified herein.

The storage device 330 is shown to include a configuration module 306 and a tool assignment module. As described above these may be implemented in other architectures besides modules and may be implemented in a single software application. The features and functions of the configuration module 306 and the tool assignment module 308 are discussed further with respect to FIGS. 4 and 5 below.

The computing device 300 also includes a communications interface 340. In some examples, the communications interface 340 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array ("FPGA") specifically to execute the various methods. For example, examples may be implemented in digital electronic circuitry, or in computer hardware, firmware, software, or in a combination thereof. In one example, a device may include a processor or processors. The processor comprises a computer-readable medium, such as a random access memory ("RAM") coupled to the processor. The processor executes processor-executable program instructions stored in memory, such as executing one or more computer programs. Such processors may comprise a microprocessor, a digital signal processor ("DSP"), an application-specific integrated circuit ("ASIC"), field programmable gate arrays ("FPGAs"), and state machines. Such processors may further comprise programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code executable to carry out one or more of the methods (or parts of methods) described herein.

Figure 4:
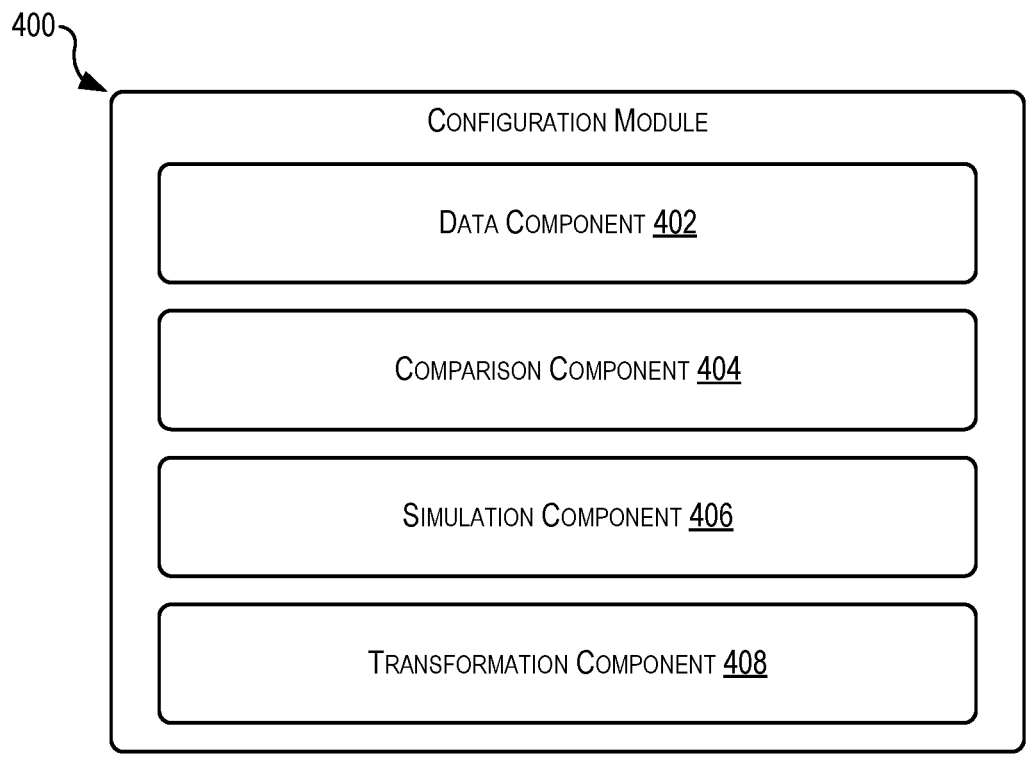
FIG. 4 illustrates a simplified block diagram depicting elements for configuring robotic arms of a surgical robot, according to at least one example.

FIG. 4 illustrates a block diagram depicting an example configuration module 400 with components to enable analysis of and aiding configuration of the surgical device 114. To this end, the configuration module 400 includes a data component 402, a comparison component 404, a simulation component 406, and a transformation component 408.

Turning now to the data component 402, the data component 402 is configured to interface with or serve as a database, such as database 202 to access data for use by the configuration module 400 including historical initial configurations, historical procedure configurations, and surgeon preferences. In some instances, the preferences may also include standards set by a hospital or a standard-setting group. The preferences may also include patient preferences, such as preferences for locations of surgical ports, which will leave scars, or preferences to avoid particular anatomy. The data component 402 alone, or in combination with a database (e.g., database 202), stores information such as the data described above and is capable of selecting data for use by the configuration module 400 based on procedure type, user identity, and other similar filters.

The comparison component 404 is configured to compare kinematic data describing the positions of the robotic arms 226 against data obtained from the database 202 such as configuration data describing the kinematics of robotic arms 226 in previous surgical procedures throughout the procedure. The configuration data includes positions and orientations of the robotic arms 226. In some examples, the comparison component 404 is configured to receive a procedure input which narrows down the database query to a subset of data from the database 202 including similar procedures to the surgical procedure to be performed. The comparison component 404 may compare angles and positions of each joint and linkage of the robotic arms 226 against stored or predicted angles and positions of each joint and linkage in the database 202. The comparison component 404 is also configured to project future configurations of the robotic arms 226 based on procedure data for the current surgical procedure such as present positions and stages in the procedure and historical data from previous similar procedures to identify and compare expected future configurations from the simulation against the configuration data and to identify potential instances of collision, as described in further detail below with respect to the simulation component 406. The comparison component 404 may further be configured to determine a configuration score based on the comparison of the kinematic data and the data from the database 202, a higher score representing a closer match of the two. For example, the comparison component 404 may compare the kinematic data to historic kinematic data from the database 102 to determine whether each of the angles of the joints in the kinematic data are within a predetermined range (such as within 1%) of the angles within the historic data. The score may be reduced for each angle which is outside if certain ranges of the historic data angles, such as within 1%, 2%, 5%, 10%, etc. In other examples, the score may be generated based on statistical data from the historical data, such as whether the present angles of the joints are within a standard deviation of the median of the historical data.

The comparison component 404 also adjusts the data describing positions and angles of the robotic arms 226 for comparison against the historical data based on patient-specific characteristics. For example, when patients of different size are operated on in the system 200, the proper positions of the robotic arms 226 will vary based on the patient size. When comparing a procedure on a patient with a low BMI versus a high BMI, the proper position of the robotic arms 226 will result in different, likely larger angles for at least some of the joints of the robotic arms 226 in the case of a patient with a higher BMI. Selecting the proper robotic arm positions for patient-specific characteristics allows direct comparison of the kinematic data to historical data from previous procedures. In one example, the robotic arm positions or the data may be selected or transformed based on the BMI or height and weight of a patient. A transformation of the proper positions may include multiplication of the positions and angles of the joints by a factor related to the patient characteristic, such as BMI. For example, a transformation of proper positions from a lower BMI data set to a higher BMI patient may include multiplying the angle of each joint by a factor greater than one.

The simulation component 406 is configured to simulate configurations of the robotic arms 226 throughout the remainder of the procedure based on a present configuration as described in the kinematic data and historical movement data for the type of surgical procedure being performed. The simulation component 406 projects future positions of the robotic arms 226 based on historical configuration data on the database 202 and proceeds to approximate or simulate the motions that will likely be performed by the robotic arms 226 through the remainder of the procedure based on data from the database 202 for the procedure type. Through this simulation, the simulation component 406 and the comparison component 404 are able to compare present and potential future or expected configurations and to identify potentially problematic future configurations of the robotic arms. For example, at a first stage of the procedure a robotic arm 226 may be in a different configuration than in previous surgeries. The simulation component 406 is configured to extrapolate and identify how the robotic arm 226 is expected to move based on of the expected course of the procedure from previous surgeries and apply those expected movements in a simulation. If the robotic arm 226, is likely to collide with anatomy or another robotic arm 226 at a later stage due to the difference at the first stage, the simulation component will identify the potential collision and provide a notification of the erroneous positioning to the user to prevent the later collision.

The transformation component 408 is configured to transform configuration data for storage on the database 202. The transformation component 408 is also configured to adjust normalized data based on patient characteristics, as described above with respect to patient BMI at the comparison component 404. For example, after a procedure is completed, configuration data from the procedure may be uploaded to the database 202 to further develop and refine the library of configurations and accepted procedure practices. For more direct comparison and interpolation, the data may be transformed based on the patient characteristics, such as BMI, described above. In some instances, the transformation component 408 may filter data based on the patient characteristic and select historical data for comparison based on the patient characteristic matching or nearly matching the patient characteristic of the present patient. This allows more direct comparison of configurations from procedures on different patients.

Though presented above with reference to a particular structure and architecture, with the module having sub-modules or components which perform various operations, the configuration module 400 may include any suitable logical or physical divisions such as separate databases, memory modules, as well as suitable combinations of hardware, software, or firmware configured to implement the functionality of the methods described herein, such as the processes 600, 700, 800, and 900 described below with respect to FIGS. 6, 7, 8, and 9.

FIG. 5 illustrates a simplified block diagram depicting a tool assignment module 500 with components to enable analysis and assignment of surgical tools for the surgical device 214, according to at least one example. The tool assignment module 500 is an example of the tool assignment module 308 described above with respect to FIGS. 1 and 2. To this end, the tool assignment module 500 includes a data component 502, a display component 504, and a comparison component 506.

Turning now to the data component 502, the data component 502 is configured to interface with or serve as a database, such as database 202 to access data to enable use by the tool assignment module 500 including initial tool assignments. The data component 502 stores information such as the data described above and is capable of selecting data for use by the tool assignment module 500 based on procedure type, user identity, and other selection options.

The display component 504 is configured to provide instructions and notifications for display at the display 218 of the surgical console 212 as well as generate a graphical interface element to display the notifications alongside with the image data 234.

The comparison component 506 is configured to compare current tool assignments of the surgical tools 228 against the database 202 and specifically against a database of tool assignments for the selected procedure. For example, the comparison component 506 may compare the current tool assignments of surgical tools 228 during setup for a procedure and notify a user that a particular tool is connected to an incorrect robotic arm, based on the database 202 or based on surgeon preferences.

Though presented above with reference to a particular structure and architecture, with the module having sub-modules or components which perform various operations, the tool assignment module 500 may include any suitable logical or physical divisions such as separate databases, memory modules, as well as suitable combinations of hardware, software, or firmware configured to implement the functionality of the methods described herein, such as the processes 600, 700, 800, and 900 described below with respect to FIGS. 6, 7, 8, and 9.

FIGS. 6-9 illustrate example flow diagrams showing processes 600, 700, 800, and 900, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent processor-executable instructions stored on one or more non-transitory computer-readable storage media that, when executed by one or more processors, perform the recited operations. Generally, processor-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

Figure 6:
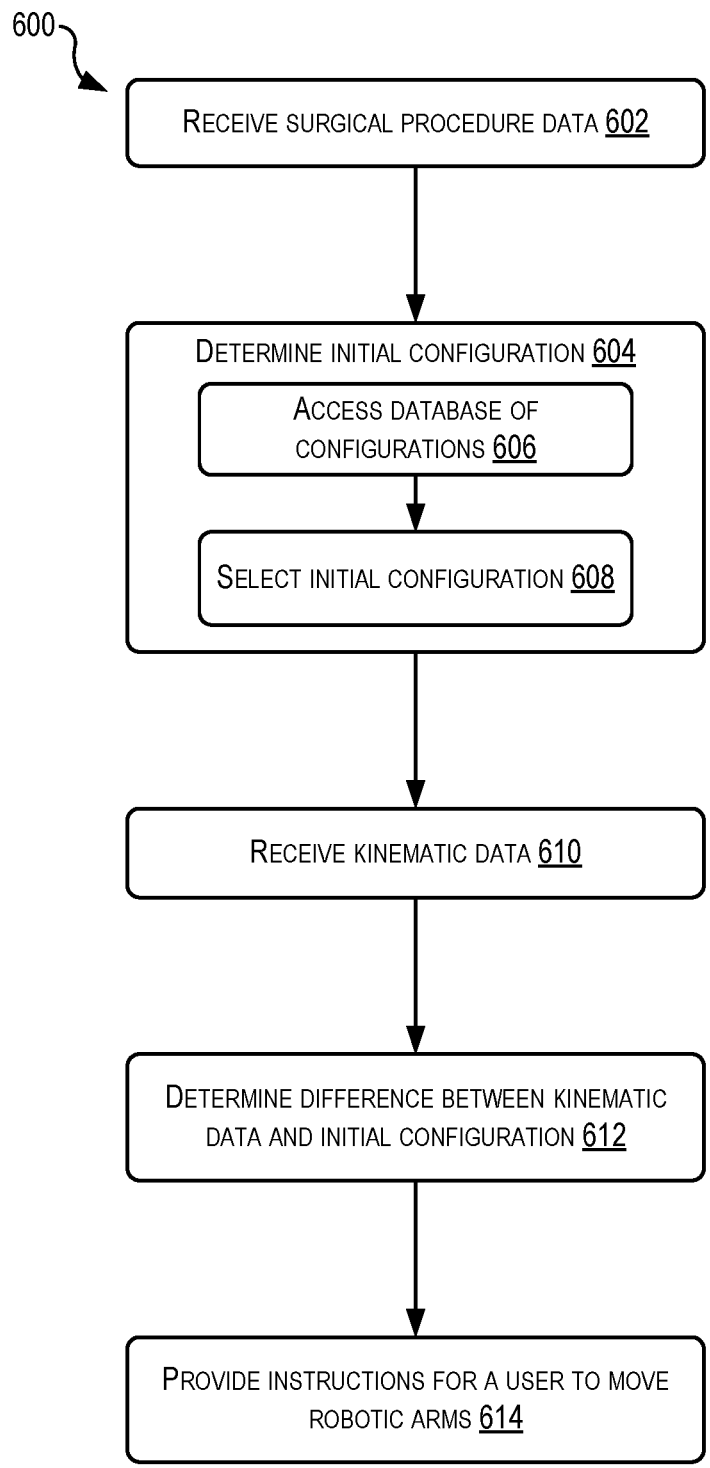
FIG. 6 illustrates an example flow chart depicting an example process for configuring a surgical robot, according to at least one example.

Turning now to FIG. 6, FIG. 6 illustrates an example flow chart depicting a process 600 for configuring a surgical device 214 at the start of and during a surgical procedure, according to at least one example. The process 600 is performed by the configuration module 306 executed within the computing device 204 and may, in some cases also be performed, at least in part, by the tool assignment module 308. The process 600 in particular corresponds to configuring the surgical device 214 to reduce the likelihood of collisions and improve the performance of robotic surgical procedures.

The process 600 begins at block 602 by the computing device 204 receiving surgical procedure data. The surgical procedure data relates to the surgical procedure to be performed and may be received from a user through a user input device of the surgical console 212 or from database 202. The surgical procedure data includes data such as the type of procedure (e.g., appendectomy, laparotomy, laparoscopy). Additionally, the surgical procedure data may include information such as patient characteristics, BMI, height, weight, or other patient dimensions.

At block 604, the computing device 204 determines an initial configuration of robotic arms 226 and surgical tools 228 connected to the robotic arms 226. Block 604 includes sub-blocks 606 and 608 for processes performed by the computing device 204 to determine the initial configuration. At sub-block 606, the computing device 204 accesses a database 202 with configuration data. The database 202 includes orientations and positions for the robotic arms 226 of the surgical device 214. Sub-block 608 includes the computing device 104 selecting initial configurations for the robotic arms 226 as well as multiple configurations for the robotic arms 226 throughout a procedure. In some instances, the computing device 204 may simulate or interpolate expected configurations in instances where the database 202 doesn't include every position for each of the kinematic arms. For example, the database 202 may include positions for a first and a second step but is missing intermediate or transitional positions which may be approximated by the simulation or interpolation.

The initial configuration is selected based on the surgical procedure data from block 602. The computing device 204 first selects a subset of the configuration data based on the procedure type from block 602 and then the computing device 204 adjusts the initial configuration based on the patient data, such as the BMI as described above with respect to FIG. 4. Selecting the initial configuration data and adjusting based on the BMI or other patient data may include other sub-processes, such as selecting a subset of the configuration data based on the patient data. For example, the computing device 204 may select a subset of the configuration data based on a match of the procedure type and a match or near match of the patient data.

In some examples, determining the initial configuration at block 604 includes implementing a machine-learning algorithm or other algorithm to estimate or approximate an initial configuration based on multiple data points within the configuration data. For instance, the configuration data may include a number of configurations for one procedure, each configuration associated with patient specific information such as BMI. Block 604 may include the computing device 204 interpolating, based on the patient data in the database, how the robotic arms 226 should be positioned. For example, a first configuration may be included in the configuration data for a patient with a BMI of 19 and a second configuration may be included in the configuration data for a patient with a BMI of 23. The patient to be operated on may have a BMI of 21, and therefore the computing device 204 may average the first and the second configurations to determine an initial configuration. In other examples, machine learning algorithms or data interpolation techniques known to those in the art may be implemented to adjust the configuration data based on the patient characteristics.

At block 610, the computing device 204 receives kinematic data from the surgical device 214 describing the current position or orientation of the robotic arms 226.

At block 612, the computing device 204 determines a difference between the kinematic data received at block 610 and the initial configuration determined at block 604. The computing device 204 compares the positions and orientations of the robotic arms 226 to identify differences along the length of the robotic arms 226 where the kinematic data and the initial configuration differ.

In response to the differences determine in block 612, at block 614 the computing device 204 provides instructions to a user, through display 218, to move the robotic arms 226 to match the kinematic data and the initial configuration. The instructions may be provided as a text element on the display 218 instructing the user which portions of the robotic arms 226 need to move in order to match the initial configuration. In some examples, an audible or other visual representation may show or present to the user how to adjust the configuration of the robotic arms 226.

In some examples, the computing device 204 may further determine a configuration score, the configuration score providing a numerical representation of how well the kinematic data and the initial configuration match. For instance, a 100% score may indicate a perfect match while a 75% score may represent only three-quarters of the configuration matching or nearly matching. The configuration score may be presented at the display 218 along with the instructions to adjust the position or orientation of the robotic arms 226.

Figure 7:
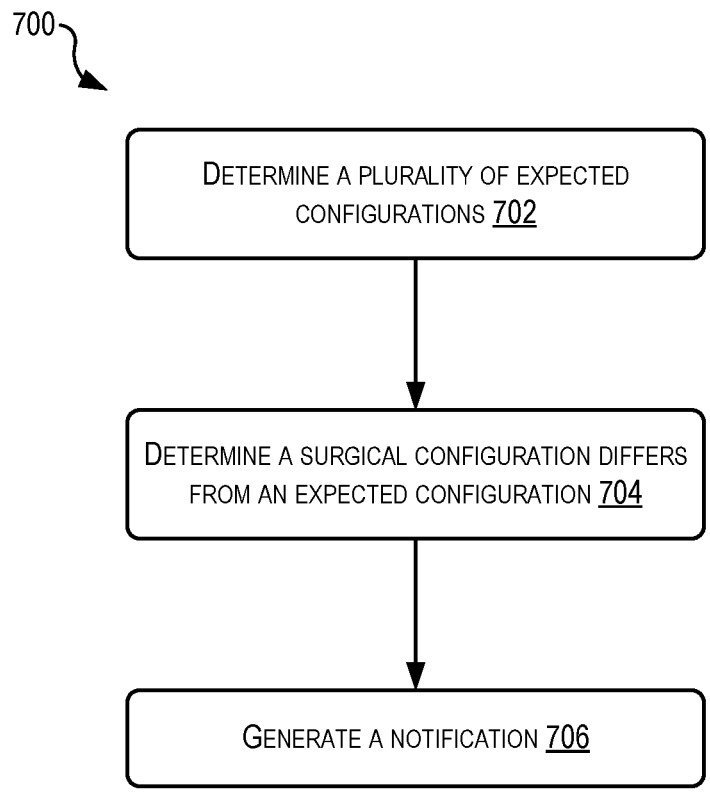
FIG. 7 illustrates an example flow chart depicting an example process for initially configuring robotic arms of a surgical robot, according to at least one example.

FIG. 7 illustrates an example flow chart depicting a process 700 for simulating expected positions of the robotic arms 226 of a surgical device 214 and comparing present kinematic data to the simulated positions, according to at least one example. The process 700 is performed by the computing device 204.

At block 702, the computing device 204 determines a plurality of expected configurations. The expected configurations represent configurations of the robotic arms 226 throughout the procedure, in advance of the present state and stage of the procedure. This may be determined by the computing device 204 based on a database of procedures, for example by selecting a subset of data including a number of sequential configurations of robotic arms 226 during a particular procedure. As described above with respect to block 604 of FIG. 6, the computing device 204 may adjust the data based on patient characteristics using any number of techniques, such as averages and machine learning techniques. In other examples, the expected configurations may be determined based on preoperative and intra operative imaging of the patient and procedure area. For instance, the computing device 204 may determine a plurality of configurations for the robotic arms 226 while avoiding particular anatomy or potential collisions. In particular, the computing device 204 may simulate the anticipated moves of the robotic arms 226 based on the procedure and historical procedure data and based on the simulation and the present configuration of the robotic arms, suggest movements of the robotic arms 226 to resolve, prevent, or minimize potential collisions during a later stage of the procedure. In some examples, the database 202 maintains different sets of data for different patient characteristics, such as age, BMI, height, gender, etc. and the expected configurations are determined by the computing device 204 accessing a dataset of the sets of data corresponding to the patient characteristics of the patient to be operated on.

At block 704, the computing device 204 determines when a surgical configuration differs from an expected configuration, including the simulated configurations described above at block 702 and the present configuration to the present configuration of the robotic arms. The difference may be an absolute difference or may be a difference which exceeds a predetermined threshold. The threshold may be based on a joint by joint difference or may be based on an overall position score or overall position of the entire arm. As described above, this determination may be used by the computing device 204 to identify potential future collisions of robotic arms 226 or configurations which may be difficult to operate, such as when a joint of the robotic arm 226 is at an end of its range of motion, and determine an adjustment to the robotic arms 226 at the present stage to resolve the future complications.

At block 706, the computing device 204 generates a notification for the user though the surgical console 212 to move the robotic arms 226 to resolve the future complications as described with respect to block 618 In some examples, the notification is presented at a different display device such as a handheld user device, a display in the surgical room that is separate from the console, etc. The notification may include a visual, auditory, or tactile notification provided to a user.

Figure 8:
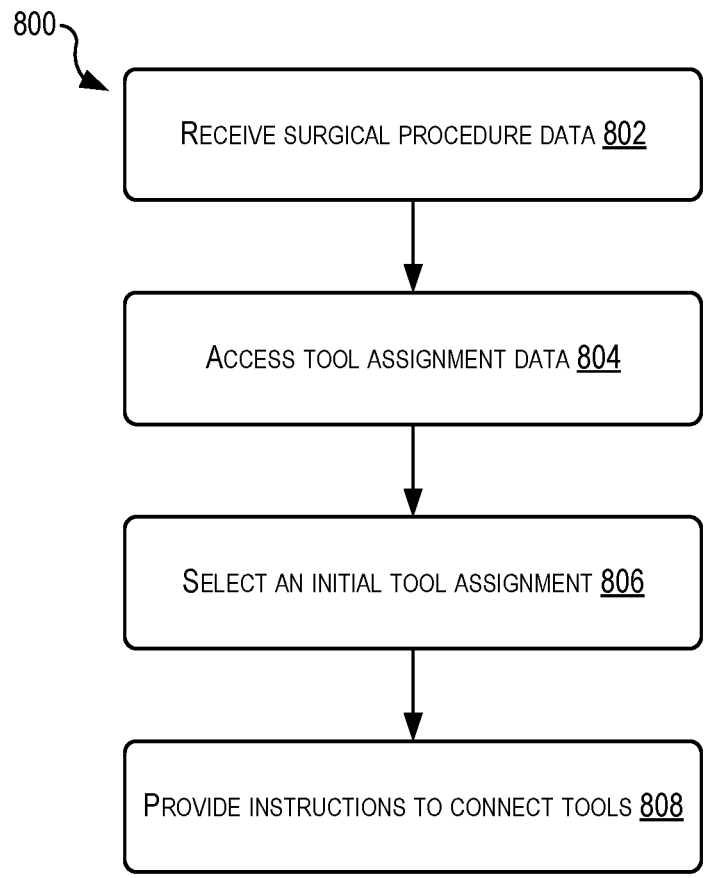
FIG. 8 illustrates an example flow chart depicting an example process for comparing a configuration of a surgical robot to previous configuration data, according to at least one example.

FIG. 8 illustrates an example flow chart depicting a process 800 for initially configuring robotic arms 226 of a surgical device 214, according to at least one example. The process 800 is performed by the computing device 204.

The process 800 begins at block 802 by the computing device 204 receiving surgical procedure data. The surgical procedure data relates to the surgical procedure to be performed and may be received from a user through a user input device of the surgical console 212 or from database 202. The surgical procedure data includes data such as the type of procedure, the location of the procedure, location of procedure ports, and other information relating to the background information of the procedure to be performed.

At block 804, the computing device 104 accesses tool assignment data on a database, such as database 202. The tool assignment data includes surgical tool 228 selections for various procedures, and may also include times or steps of the procedure when the surgical tools 228 are exchanged for other surgical tools 228.

At block 806, the computing device 204 selects an initial tool assignment for the surgical tools 228 to be connected to the robotic arms 226 by the user. The initial tool assignment is selected based on the procedure type, the procedure type defining the surgical tools 228 required. Additionally, the computing device 204 may select the initial tool assignment based on user preferences, such as a surgeon's preferred surgical tool 228 selection.

At block 808, the computing device 204 provides instructions to connect surgical tools 228 to the robotic arms 226. The instructions identify the surgical tools selected at block 806 as well as the robotic arm 226 each surgical tool 228 connects to. The instructions are provided to the user through the surgical console 212 and specifically at the display 218, where the instructions are displayed as text.

The process 800 may also include a confirmation step to confirm the surgical tools 228 attached to the robotic arms 226 match the instructions provided to the user. For example, the computing device 204 may provide an additional query to the user to confirm each of the surgical tools 228 connected to the robotic arms 226 one at a time. In some examples the computing device 204 may detect an identity of the surgical tools 228 connected through the use of electronic identification, such as with radio-frequency identification (RFID), unique visual identifiers, or electronic markers which produce a unique signal readable by the computing device 204 when the surgical tool 228 is connected to the robotic arm 226 to automatically confirm the attachment of the surgical tools 228 matches the instructions provided to the user.

Figure 9:
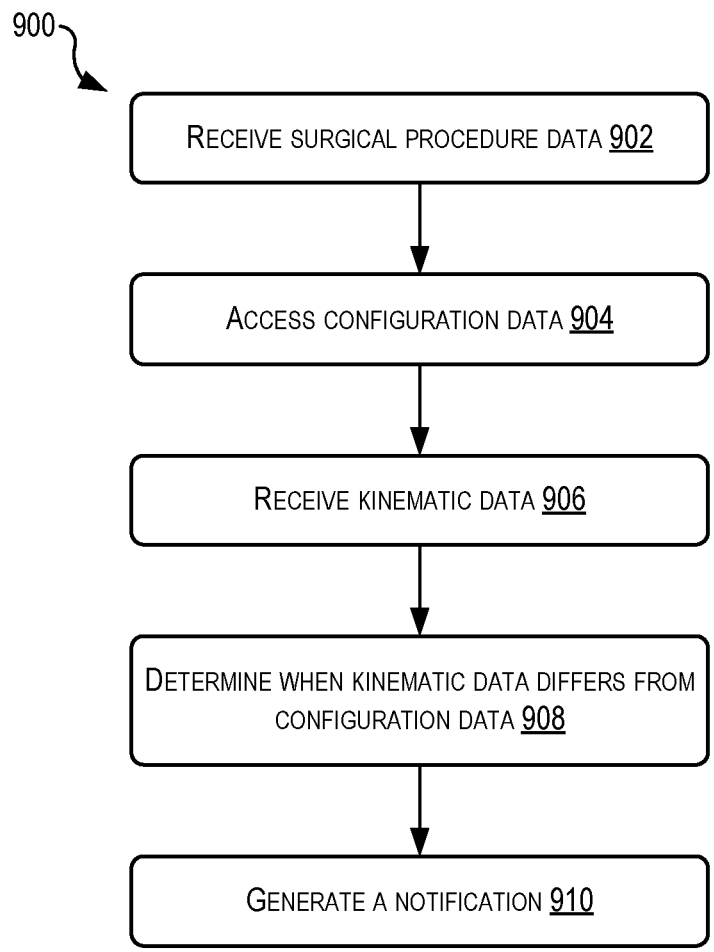
FIG. 9 illustrates an example flow chart depicting an example process for comparing a configuration of a surgical device to previous configuration data to identify deviations from a surgical procedure.

FIG. 9 illustrates an example flow chart depicting a process 900 for comparing a configuration of a surgical device 214 to previous configuration data, according to at least one example. The process 900 is performed by the computing device 204 (FIG. 1). The process 900 in particular corresponds to comparing kinematic data describing the configuration of the robotic arms 226 to configuration data describing previous or approved configurations of the robotic arms 226 during the surgical procedure.

The process 900 begins at block 802 by the computing device 204 receiving surgical procedure data. The surgical procedure data may be received from a user through a user input device of the surgical console 212 or from database 202. The surgical procedure data includes data such as the type of procedure.

At block 904, the computing device 204 accesses configuration data from a database of configurations. The database of configurations includes orientations and positions for the robotic arms 226 of the surgical device 214. Block 904 also includes the computing device 204 selecting an initial configuration for the robotic arms 226 as described in FIG. 6 above. The initial configuration is selected based on the surgical procedure data from block 902.

At block 906, the computing device 204 receives kinematic data from the surgical device 214 describing the current positions or orientations of the robotic arms 226.

At block 908, the computing device 204 determines when the kinematic data differs by more than a threshold amount from the configuration data selected at block 904. The threshold amount may be within a certain range, such as less than a standard deviation, less than a partial standard deviation, a percentage of joint angles, or other measures. This may include the computing device 204 comparing the positions and orientations of the robotic arms 226 to identify joints of the robotic arms 226 where the kinematic data describing the angle of the joints and the joint angles from the historical data differ. In some examples the computing device 204 compares the configuration data, including the simulated configurations described above at block 616 with the kinematic data and a simulation of the present procedure as the user may perform the procedure, the simulation based on previous procedures. As described above, this difference may be used by the computing device 204 to identify potential future collisions of robotic arms 226 or difficult configurations and determine an adjustment to the robotic arms 226 at the present stage to resolve the future complications.

At block 910, the computing device 204 generates a notification for the user though the surgical console 212 to move the robotic arms 226 to resolve the future complications as described above. The user inputs instructions at the surgical console 212 based on the notification. For example, the notification may inform the user that a particular robotic arm 226 is out of position, and also include information such as instructing the user to move the robotic arm 226 into position by adjusting the position of a particular joint of the robotic arm 226.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A computer-implemented method, comprising:
   receiving, by a computing device, data corresponding to a surgical procedure associated with a robotic surgical system, the robotic surgical system comprising a plurality of robotic arms;
   determining, by the computing device, an initial configuration for each of the plurality of robotic arms by at least:
   accessing a dataset of configurations corresponding to a plurality of surgical procedures;
   selecting the initial configuration based on the surgical procedure and the dataset of configurations, the initial configuration defining an initial position and orientation; and
   selecting an initial tool selection for each robotic arm of the plurality of robotic arms before beginning the surgical procedure based on a type of the surgical procedure;
   receiving kinematic data corresponding to a state of each of the plurality of robotic arms;
   determining, by the computing device, a plurality of configurations for each of the plurality of robotic arms during the surgical procedure by comparing a current configuration to historical configuration data, wherein:
   the historical configuration data comprises statistical patterns and surgical outcomes; and
   individual robotic arm configurations of the plurality of configurations define one or more of (1) positions of each joint of the plurality of robotic arms, (2) orientations of each joint of the plurality of robotic arms, or (3) tool selections for the plurality of robotic arms during the surgical procedure;
   determining, during the surgical procedure, that a configuration of the robotic surgical system differs from at least one expected robotic arm configuration of a dataset comprising a plurality of expected robotic arm configurations; and
   generating a configuration notification relating to the configuration differing from the at least one expected robotic arm configuration.

2. The computer-implemented method of claim 1, further comprising:
   receiving interchangeable tool data corresponding to an assignment of interchangeable tools to the plurality of robotic arms;
   comparing the interchangeable tool data to a tool configuration of the plurality of robotic arms during the surgical procedure; and
   generating a tool notification when the interchangeable tool data differs from the tool configuration.

3. The computer-implemented method of claim 1, wherein determining that the configuration of the robotic surgical system differs from the at least one expected robotic arm configuration is based on the kinematic data.

4. The computer-implemented method of claim 3, wherein determining that the configuration of the robotic surgical system differs from the at least one expected robotic arm configuration is further based on determining that the kinematic data is within a predetermined range.

5. The computer-implemented method of claim 1, further comprising receiving patient data corresponding to characteristics of a patient; and
   adjusting the plurality of expected robotic arm configurations based on the patient data.

6. The computer-implemented method of claim 5, wherein determining the plurality of configurations, determining that the configuration of the robotic surgical system differs from at least one configuration, and generating the configuration notification each occur after a beginning of the surgical procedure.

7. The computer-implemented method of claim 1, further comprising:
   instructing movement of the plurality of robotic arms when the configuration of the robotic surgical system differs from the at least one expected robotic arm configuration.

8. The computer-implemented method of claim 1, further comprising generating a position score based on the configuration of the robotic surgical system differing from the at least one expected robotic arm configuration.

9. The computer-implemented method of claim 8, wherein the at least one expected robotic arm configuration is a historic robotic arm configuration, and the position score is based on a percent difference between the configuration of the robotic surgical system and the historical robotic arm configuration.

10. The computer-implemented method of claim 1, further comprising:
    determining a difference between the state of each of the plurality of robotic arms and the initial configuration based on the kinematic data; and
    providing instructions to a user, based on the difference, for movement of each robotic arm of the plurality of robotic arms into the initial configuration.

11. A robotic surgical system comprising:
    a plurality of robotic arms;
    a user interface;
    one or more processors; and
    one or more non-transitory computer-readable media comprising processor-executable instructions that, when executed by the one or more processors, cause the one or more processors to:
    receive data corresponding to a surgical procedure performable by the plurality of robotic arms;
    determine, by the one or more processors, an initial configuration for each of the plurality of robotic arms by at least:
    accessing a dataset of configurations corresponding to a plurality of surgical procedures;

selecting the initial configuration based on the surgical procedure and the dataset of configurations, the initial configuration defining an initial position and orientation; and selecting an initial tool selection for each robotic arm of the plurality of robotic arms before beginning the surgical procedure based on a type of the surgical procedure;

receive kinematic data corresponding to a state of each of the plurality of robotic arms;

determine, by the one or more processors, a plurality of configurations for each of the plurality of robotic arms during the surgical procedure by comparing a current configuration to historical configuration data, wherein:
the historical configuration data comprises statistical patterns and surgical outcomes; and
individual robotic arm configurations of the plurality of configurations define one or more of (1) positions, (2) orientations, or (3) tool selections for the plurality of robotic arms during performance of the surgical procedure;

determine, during the surgical procedure, that a configuration of the plurality of robotic arms differs from at least one expected configuration of a dataset comprising a plurality of expected configurations; and generate a configuration notification for presentation at the user interface, the configuration notification relating to the configuration differing from the at least one expected configuration.

12. The robotic surgical system of claim 11, wherein the one or more non-transitory computer-readable media further comprise additional processor-executable instructions that, when executed by the one or more processors, cause the one or more processors to:
access an outcome dataset of configurations and corresponding patient outcomes for surgical procedures; and
provide, for presentation at a user notification device, an outcome for the configuration of the robotic arms from the outcome dataset.

13. The robotic surgical system of claim 11, wherein the dataset of configurations comprises a plurality of tool arrangements and orientations of the plurality of robotic arms during the surgical procedure.

14. The robotic surgical system of claim 11, wherein the one or more non-transitory computer-readable media further comprise additional processor-executable instructions that, when executed by the one or more processors, cause the one or more processors to:
receive patient data corresponding to characteristics of a patient; and
adjusting the plurality of configurations based on the patient data.

15. The robotic surgical system of claim 11, wherein the dataset of configurations comprises surgeon preferences, and selecting the initial configuration is based on the surgeon preferences.

16. The robotic surgical system of claim 11, wherein the one or more non-transitory computer-readable media further comprise additional processor-executable instructions that, when executed by the one or more processors, cause the one or more processors to:
determine a difference between the state of each of the plurality of robotic arms and the initial configuration based on the kinematic data; and
provide instructions to a user, based on the difference, for movement of each robotic arm of the plurality of robotic arms into the initial configuration.

17. A non-transitory computer-readable medium storing instructions that, when executed by one or more processors, cause the one or more processors to perform operations including:
receiving, by a computing device, data corresponding to a surgical procedure associated with a robotic surgical system, the robotic surgical system comprising a plurality of robotic arms;
determining, by the computing device, an initial configuration for each of the plurality of robotic arms by at least:
accessing a dataset of configurations corresponding to a plurality of surgical procedures;
selecting the initial configuration based on the surgical procedure and the dataset of configurations, the initial configuration defining an initial position and orientation; and
selecting an initial tool selection for each robotic arm of the plurality of robotic arms before beginning the surgical procedure based on a type of the surgical procedure;
receiving kinematic data corresponding to a state of each of the plurality of robotic arms;
determining, by the computing device, a plurality of configurations for each of the plurality of robotic arms during the surgical procedure by comparing a current configuration to historical configuration data, wherein:
the historical configuration data comprises statistical patterns and surgical outcomes; and
individual robotic arm configurations of the plurality of configurations define one or more of (1) positions of each joint of the plurality of robotic arms, (2) orientations of each joint of the plurality of robotic arms, or (3) tool selections for the plurality of robotic arms during the surgical procedure;
determining, during the surgical procedure, that a configuration of the robotic surgical system differs from at least one expected robotic arm configuration of a dataset comprising a plurality of expected robotic arm configurations; and
generating a configuration notification relating to the configuration differing from the at least one expected robotic arm configuration.

18. The non-transitory computer-readable medium of claim 17, further comprising instructions that, when executed by one or more processors, cause the one or more processors to perform operations including:
determining a difference between the state of each of the plurality of robotic arms and the initial configuration based on the kinematic data; and
providing instructions to a user, based on the difference, for movement of each robotic arm of the plurality of robotic arms into the initial configuration.

19. The non-transitory computer-readable medium of claim 17, further comprising instructions that, when executed by one or more processors, cause the one or more processors to perform operations including:
receiving interchangeable tool data corresponding to an assignment of interchangeable tools to the plurality of robotic arms;
comparing the interchangeable tool data to a tool configuration of the plurality of robotic arms during the surgical procedure; and
generating a tool notification when the interchangeable tool data differs from the tool configuration.

20. The non-transitory computer-readable medium of claim 17, further comprising instructions that, when executed by one or more processors, cause the one or more processors to perform operations including:
- access an outcome dataset of configurations and corresponding patient outcomes for surgical procedures; and
- provide, for presentation at a user notification device, an outcome for the configuration of the robotic arms from the outcome dataset.

21. The non-transitory computer-readable medium of claim 17, wherein determining the plurality of configurations, determining that the configuration of the robotic surgical system differs from at least one configuration, and generating the configuration notification each occur after a beginning of the surgical procedure and further comprising instructions that, when executed by one or more processors, cause the one or more processors to perform operations including:
- receiving patient data corresponding to characteristics of a patient; and
- adjusting the plurality of expected robotic arm configurations based on the patient data.

22. The non-transitory computer-readable medium of claim 17, further comprising instructions that, when executed by one or more processors, cause the one or more processors to perform operations including:
- receive patient data corresponding to characteristics of a patient; and
- adjusting the plurality of configurations based on the patient data.

* * * * *